(12) United States Patent
Osten et al.

(10) Patent No.: US 10,257,901 B2
(45) Date of Patent: Apr. 9, 2019

(54) LED DENTAL LIGHT SOURCE WITH VARIABLE CHROMATICITY AND METHOD

(71) Applicant: OSRAM GmbH, Munich (DE)

(72) Inventors: Andreas Osten, Cambridge, MA (US); Jack L. Burwick, York, PA (US)

(73) Assignee: OSRAM GMBH, Munich (DE)

( * ) Notice: Subject to any disclaimer, the term of this patent is extended or adjusted under 35 U.S.C. 154(b) by 695 days.

(21) Appl. No.: 14/475,628

(22) Filed: Sep. 3, 2014

(65) Prior Publication Data

US 2016/0061390 A1    Mar. 3, 2016

(51) Int. Cl.
| | |
|---|---|
| A61B 1/06 | (2006.01) |
| F21K 9/64 | (2016.01) |
| A61C 13/15 | (2006.01) |
| H05B 33/08 | (2006.01) |
| F21Y 113/13 | (2016.01) |
| F21Y 115/10 | (2016.01) |
| F21W 131/202 | (2006.01) |

(52) U.S. Cl.
CPC ....... *H05B 33/0857* (2013.01); *A61B 1/0638* (2013.01); *A61B 1/0646* (2013.01); *A61B 1/0653* (2013.01); *A61B 1/0684* (2013.01); *A61C 19/003* (2013.01); *F21K 9/64* (2016.08); *F21W 2131/202* (2013.01); *F21Y 2113/13* (2016.08); *F21Y 2115/10* (2016.08)

(58) Field of Classification Search
CPC ..... F21K 9/56; F21V 9/00; F21V 9/10; A61C 19/003; A61C 19/004; H05B 33/0857; A61B 1/0638; A61B 1/0646; A61B 1/0653; A61B 1/0684
USPC .................................................. 433/29, 114
See application file for complete search history.

(56) References Cited

U.S. PATENT DOCUMENTS

| | | | |
|---|---|---|---|
| 8,016,470 B2 | 9/2011 | Li et al. | |
| 2002/0151941 A1* | 10/2002 | Okawa | A61B 19/52 607/99 |
| 2003/0215766 A1* | 11/2003 | Fischer | A61C 19/004 433/29 |

(Continued)

FOREIGN PATENT DOCUMENTS

| | | |
|---|---|---|
| CA | 2878349 A1 | 1/2014 |
| DE | 202004001189 U1 | 8/2004 |

(Continued)

OTHER PUBLICATIONS

International Search Report based on Application No. PCT/EP2015/069480(6 Pages) dated Nov. 5, 2015.

*Primary Examiner* — Erin Kryukova
(74) *Attorney, Agent, or Firm* — Viering, Jentschura & Partner MBB (57) ABSTRACT

A dental light having an array of light emitting diode (LED) assemblies, at least one first LED assembly having at least one first LED element configured to emit light according to a first spectral distribution, a conversion phosphor configured to convert at least a portion of the first spectral distribution. At least one filter is fixed within said converted light, the filter configured to block at least a portion thereof. The array includes at least one second LED element configured to emit light according to a second spectral distribution, wherein light having the filtered spectral distribution is selectively emitted from said array in a first mode and from both the filtered and second spectral distributions in a second mode.

7 Claims, 4 Drawing Sheets

(56) References Cited

U.S. PATENT DOCUMENTS

| | | | |
|---|---|---|---|
| 2003/0218880 A1* | 11/2003 | Brukilacchio | A61N 5/062 362/293 |
| 2004/0248059 A1* | 12/2004 | Katsuda | A61C 19/004 433/29 |
| 2005/0003323 A1* | 1/2005 | Katsuda | A61B 1/00089 433/29 |
| 2007/0184402 A1* | 8/2007 | Boutoussov | A61C 1/0046 433/29 |
| 2008/0002402 A1* | 1/2008 | Mandikos | A61C 19/003 362/231 |
| 2009/0108269 A1* | 4/2009 | Negley | H01L 27/156 257/88 |
| 2010/0118374 A1 | 5/2010 | Quach | |
| 2010/0207134 A1* | 8/2010 | Tanaka | F21K 9/00 257/89 |
| 2013/0101953 A1 | 4/2013 | Stone et al. | |
| 2013/0120688 A1* | 5/2013 | Chao | F21V 11/00 349/62 |
| 2013/0294103 A1 | 11/2013 | Li et al. | |
| 2013/0344456 A1* | 12/2013 | Jessop | A61C 19/004 433/29 |
| 2015/0034980 A1* | 2/2015 | Windisch | H01L 27/15 257/89 |
| 2015/0250572 A1 | 9/2015 | Gramann et al. | |

FOREIGN PATENT DOCUMENTS

| | | |
|---|---|---|
| EP | 2587128 A1 | 5/2013 |
| WO | 2009045223 A1 | 4/2009 |
| WO | 2013135516 A1 | 9/2013 |
| WO | 2014043488 A1 | 3/2014 |

\* cited by examiner

LED DENTAL LIGHT SOURCE WITH VARIABLE CHROMATICITY AND METHOD

TECHNICAL FIELD

Various embodiments relate generally to a device and method for providing a variable chromaticity. More particularly, various embodiments relate to a source of illumination for a dental operating theater.

BACKGROUND

Dentists use composite filling material which cures under the influence of electromagnetic radiation in the wavelength range from approx. 380 nm to approx. 500 nm, especially in the violet/blue wavelength range from 405 nm to approx. 460 nm. While blue light is required to start and to drive the curing process of the filling material, blue light in the operating environment can interfere with the application of the filling material, as the blue light can significantly shorten the working time of the material due to premature curing.

Some dental lights offer a so-called "non-curing mode feature" in which blue light is excluded from the output of the non-curing mode. A second, or normal illumination mode, may provide white light including blue spectral output. Where light emitting diodes (LEDs) are used to provide the light source for such a dental light, multiple color LEDs (e.g. red, green and blue) generate the white light, and a non-curing mode is achieved by switching off or turning down the blue LED resulting in low quality light having a low color rendering index. Furthermore, systems using multiple color LEDs require frequent recalibration of the LED intensities over time to maintain the quality of white light in the normal mode.

Differences in lumen depreciation are typical in an LED system using RGB to produce white light. In particular, the intensity of each of the red, green and blue LED elements degrade at different rates, with the result that the proportion of each color in an RGB system tend to change over time. This results in undesirable or unpleasant color (e.g. off the black body curve) and/or a reduction in the quality of the white light. For example, a color rendering index (CRI) is a proxy for light quality, wherein a CRI of 100 is considered identical to natural lighting. Deviations in the lumen depreciation profiles of multi-color LED systems therefore lead to CRI values substantially below 100 unless expensive color correction schemes are employed to counteract the effects of the depreciation.

SUMMARY

According to an embodiment of the present disclosure, a variable chromaticity light source, particularly a dental light is disclosed having an array of light emitting diode (LED) assemblies, the array including at least one first LED assembly configured to emit a first channel of visible light according to a first spectrum, the first LED assembly having a first spectral power depreciation profile, and at least one second LED assembly configured to emit a second channel of visible light according to a second spectrum. The second LED assembly has a second spectral power depreciation profile. As disclosed, the first spectrum is different from the second spectrum, and the ratio of the first spectral power depreciation profile to the second spectral power depreciation profile is substantially constant over a lifetime of said light source.

A light source is further disclosed wherein the first spectral power depreciation profile and the second spectral power depreciation profile are substantially similar with respect to at least one operational stress, and where said at least one operational stress is chosen from a group including junction temperature, environmental temperature and current density.

A light source is further disclosed wherein said at least one first LED assembly and said at least one second LED assembly respectively have a lumen maintenance value ($L_m$) being calculated according to the formula $L_m = L_a/L_n$, where $L_n$ is the nominal output of a respective LED assembly and $L_a$ is the actual output of a respective LED assembly, and said spectral power depreciation profile being the value of $L_m$ measured over said lifetime.

A light source is further disclosed wherein said lifetime extends until $L_m < 70$ in at least one of said first and second LED assembly.

A light source is further disclosed wherein the difference in a lumen maintenance value for the first LED assembly ($L1_m$) deviates by no more than 30% from the lumen maintenance value for the second LED assembly ($L2_m$) at any given time.

A light source is further disclosed wherein the first LED assembly comprises at least one LED element and the second LED assembly comprises at least one LED element, and wherein $L1_m$ and $L2_m$ are test values of said LED elements, respectively.

A light source is further disclosed wherein the at least one operational stress is chosen from a group including junction temperature, environmental temperature and junction current, and wherein a measured value for said at least one operational stress is within normal operating ranges for said light source.

A light source is further disclosed wherein the first LED assembly further comprises a phosphor converter operatively coupled to the first LED element.

A light source is further disclosed wherein the first LED assembly further comprises a filter operatively coupled to the first LED element.

A light source is further disclosed wherein the first LED element is a blue LED and the phosphor converter, preferably a yellow phosphor, at least partially converts an output of the first LED element into a white light.

A light source is further disclosed wherein said white light includes at least a first component of blue light.

A light source is further disclosed wherein the white light has a high color rendering index (CRI).

A light source is further disclosed wherein the CRI is at least 90.

A light source is further disclosed wherein said filter at least partially blocks said first component of blue light.

A light source is further disclosed wherein the filter is a dichroic filter.

A light source is further disclosed wherein the second LED element is a blue LED.

The light source as disclosed may advantageously further include a first power lead connected to each of said at least one first LED assembly, and a second power lead connected to each of said at least one second LED assembly, wherein said first power lead and said second power lead may be independently selectively connected to a source of power.

A light source is further disclosed wherein said array mixes light of said first channel of visible light with the visible light of said second channel.

A light source is further disclosed wherein said second channel of visible light includes a second component of blue light.

A light source is further disclosed wherein said first component of blue light is proportional to said second component of blue light.

A light source is further disclosed wherein said first channel of visible light and said second channel of visible light mix to produce a white light emitted from said array.

A light source is further disclosed wherein the white light emitted from said array has a high color rendering index (CRI).

A light source is further disclosed wherein the CRI is at least 90.

A light source is further disclosed wherein the at least one first LED element and the at least one second LED element are substantially functionally identical.

A light source is further disclosed wherein the at least one first LED element and the at least one second LED element are blue LED elements.

A light source is further disclosed wherein said first channel of visible light includes essentially no blue light in the wavelength range of 380-450 nm.

According to a further embodiment of the present disclosure, a dental light is disclosed including at least an array of light emitting diode (LED) assemblies, the array including at least one first LED assembly with at least one first LED element configured to emit a first light according to a first spectral distribution, at least one conversion phosphor fixed within said first light, the conversion phosphor configured to convert at least a portion of said first spectral distribution to a converted spectral distribution of light, at least one filter fixed within said converted spectral distribution of light, the filter configured to block at least a portion of the converted spectral distribution to emit a filtered spectral distribution of light, and a first power lead connected to said at least one first assembly LED element. According to the embodiment, at least one second LED assembly is disclosed including at least one second LED element configured to emit light according to a second spectral distribution, and a second power lead connected to said at least one second LED element. The light having the filtered spectral distribution is emitted from said array when said first power lead is connected to a power source, and light having a combined spectral distribution comprising the filtered and second spectral distributions is emitted when both first and second power leads are connected to a power source.

A dental light is further disclosed wherein said first LED element is a blue LED.

A dental light is further disclosed wherein said second LED element is a blue LED.

A dental light is further disclosed wherein said filter is configured to block light having the second spectral distribution.

A dental light is further disclosed wherein the filter is a dichroic filter.

A dental light is further disclosed wherein the first LED element and the second LED element are substantially functionally identical.

A dental light is further disclosed wherein the first spectral distribution and the second spectral distribution are substantially identical.

A dental light is further disclosed wherein the filter is configured to block light in the range 380-450 nm.

A dental light is further disclosed wherein the converted spectral distribution and the combined spectral distribution are substantially identical.

A dental light is further disclosed wherein the combined spectral distribution is a white light.

A dental light is further disclosed wherein the white light has a high color rendering index (CRI).

A dental light is further disclosed wherein the CRI is at least 90.

A dental light is further disclosed wherein the first and second LED assemblies are affixed to a printed circuit board. The material of the printed circuit board can be rigid and/or flexible.

According to a further embodiment of the present disclosure, a method for providing chromatically stable illumination is disclosed, including providing a first channel of visible light via at least one first light emitting diode (LED) assembly having a first light output intensity at a first light emission spectrum, and a first spectral power depreciation profile describing the output intensity over a total lifetime of the LED assembly. The method also includes selecting an effective lifetime within said total lifetime, and selecting at least one second LED assembly to provide a second channel of visible light, the second LED assembly having a second light output intensity at a second light emission spectrum different from said first emission spectrum, and a second spectral power depreciation profile describing the intensity of the second light output, the second spectral power depreciation profile substantially similar to said first spectral power depreciation profile, during at least said effective lifetime. The method further advantageously include adding, selectively, the second light channel to the first light channel.

According to the disclosed method, said adding of the second light channel with the first light channel may produce light according to a third light emission spectrum.

According to the disclosed method the third light emission spectrum may be white light.

According to the disclosed method the white light may have a high color rendering index (CRI).

According to the disclosed method the CRI may be at least 90.

According to the disclosed method the first emission spectrum may include essentially no blue light in the wavelength range 380-450 nm.

According to the disclosed method the second emission spectrum may be essentially blue light in the wavelength range 380-450 nm.

The disclosed method may further include positioning the at least one first LED assembly and the at least one second LED assembly operatively proximate to each other.

The disclosed method may further include providing, within the first LED assembly a first LED element having a first primary light emission, coupling the first LED element operatively to a converter element, converting said first primary light emission via the converter element to a converted light emission, and providing the converted light emission as said first channel of visible light.

According to the disclosed method the converter element may further include a phosphor converter, especially a Ce:YAG yellow phosphor converter.

According to the disclosed method the converter element may include a filter operatively coupled to the phosphor converter.

According to the disclosed method the first LED element may be a blue LED.

According to the disclosed method the phosphor converter may convert the first primary light emission to a white light including at least a component of the first primary light emission.

According to the disclosed method the filter may block at least a portion of said component of the first primary light emission.

According to the disclosed method the filter may be a dichroic filter.

The disclosed method may further include providing within the second LED assembly includes a second LED element having a second primary light emission.

According to the disclosed method the second LED element may be a blue LED, the second primary light emission comprises the second channel of visible light.

According to the disclosed method the first LED element and the second LED element may be substantially functionally identical.

According to the disclosed method light blocked by the filter may be supplied in substantially equal chromaticity and intensity by the second channel of visible light.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The words "spectrum", "emission spectrum" or "spectral distribution" are used herein to denote a distribution of wavelengths of light, typically visible light, in which case these terms are generally interchangeable.

Figure 1:
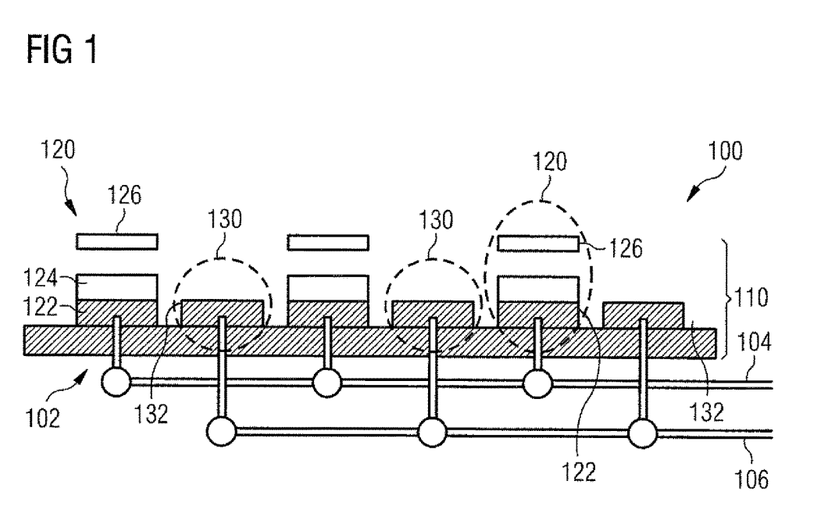
FIG. 1 is a cross-sectional representation of a lighting array according to embodiments of a light source/dental light of the present disclosure.

FIG. 1 discloses an exemplary embodiment of a variable chromaticity light source 100 comprising an array 110 of light emitting diode (LED) assemblies 120, 130. Array 110 includes a plurality of first LED assemblies 120 positioned at intervals on a printed circuit board (PCB) 102. First LED assemblies 120 are electrically connected respectively to first power lead 104.

Figure 2A:
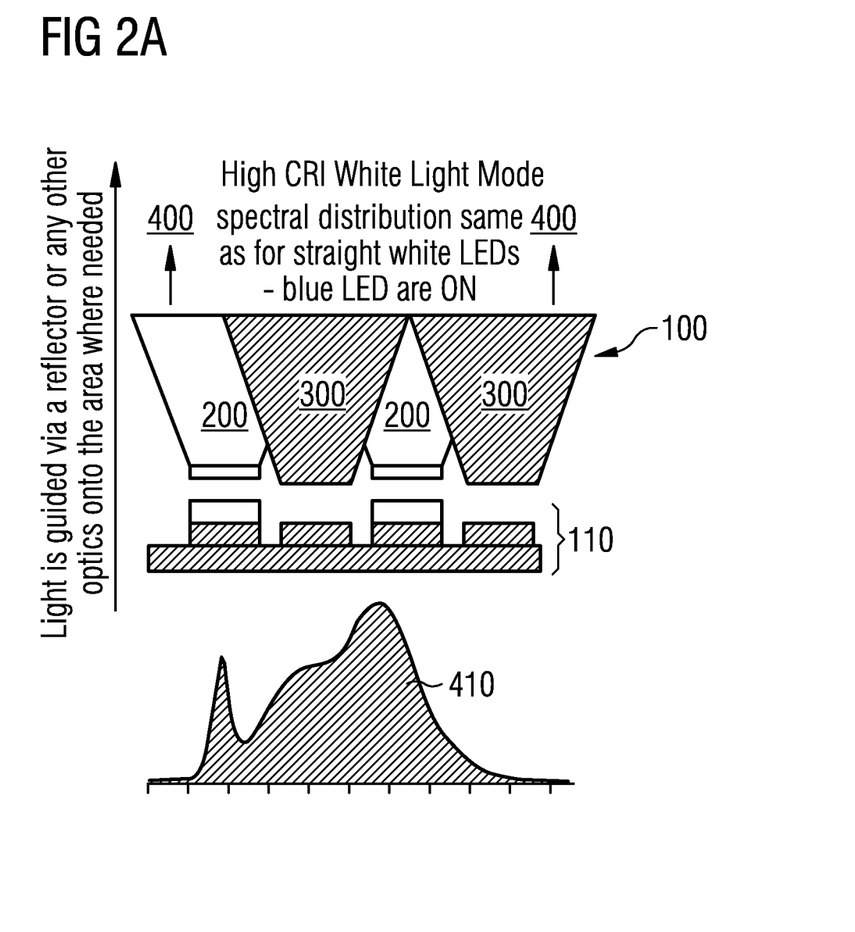
FIG. 2A and FIG. 2B show, respectively, outputs in two different modes of operation of embodiments of the present disclosure.
Figure 2B:
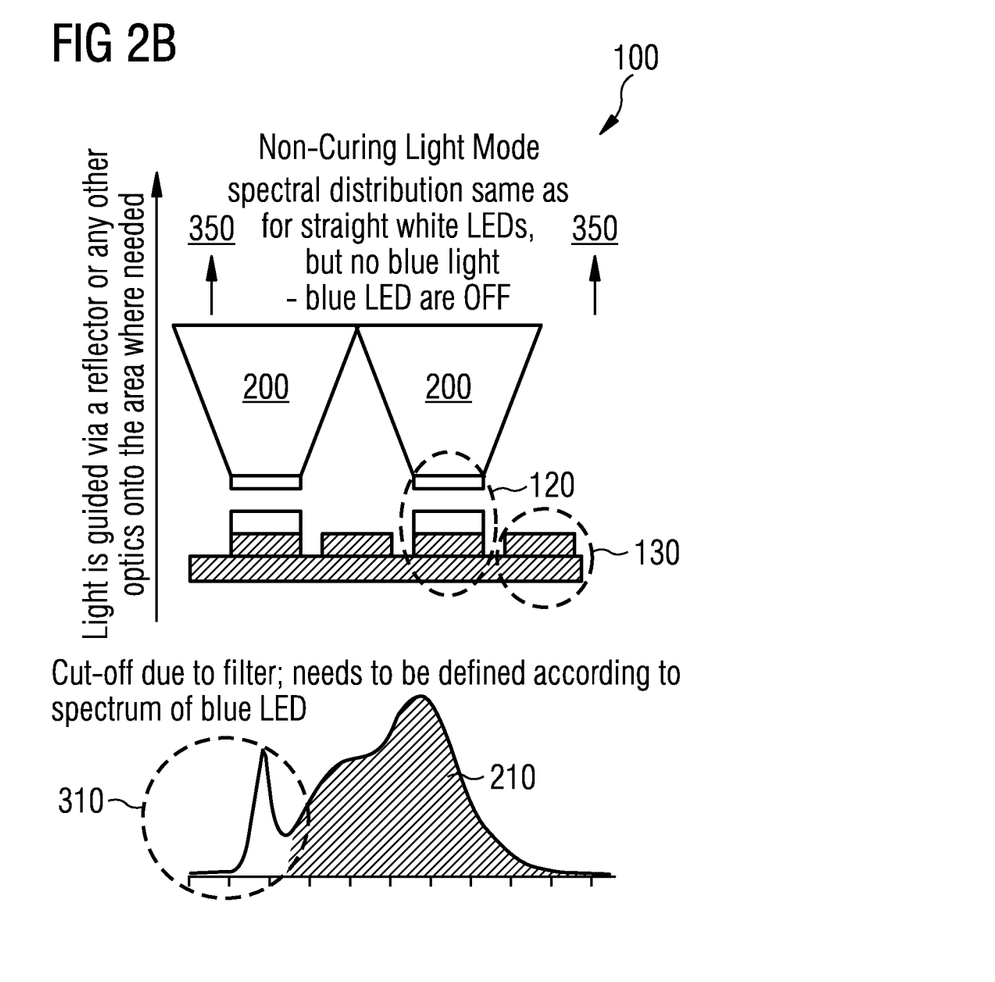

As a unit, each first LED assembly 120 is configured to emit a first channel of visible light 200 (FIG. 2A, 2B) according to a first spectrum/spectrum distribution 210 (FIG. 2B). An advantageous embodiment of assembly 120 includes phosphor-converted white light LEDs (for example, a blue LED with yellow phosphor) and may include a subsequent filter to filter out wavelengths in the blue spectrum.

A plurality of second LED assemblies 130 are likewise shown positioned at intervals on PCB 102. In particular, second LED assemblies 130 are shown advantageously alternating in position relative to first LED assemblies 120. Advantageously, alternation may be interdigitated or accomplished in other geometrical arrangements such as a tessellation of a surface. A second power lead 106 is electrically connected to each of second LED assemblies 130, respectively.

As a unit, each second LED assembly 130 is configured to emit a second channel of visible light 300 (FIG. 2A) according to a second spectrum/spectral distribution 310 (FIG. 2B) different from first spectrum 210. Advantageously, such light may be in the blue/violet spectral range down to approximately 380 nm.

During operation in an exemplary mode, electrical current applied to first power lead 104 results in emission of light according to first visible light channel 200/emission spectrum 210 (after filtering) as illustrated for example in FIG. 2B. As shown, filtered spectrum 210 lacks wavelengths in the visible blue/violet range, with the result that light channel 200 may be perceived as yellow tinted, or orange tinted as opposed to white, as such light would be appropriate to an environment where light-curable materials are being worked, such as in a dental operatory. However, depending upon the environment in which light source 100 is employed and the used composite fillings, spectrum 210 may be chosen to have any appropriate or desired spectral distribution.

During operation in a second exemplary mode, by applying current to second power lead 106 in addition to first power lead 104, both first visible light channel 200 (at spectrum 210) and second visible light channel 300 at spectrum 310 are emitted from light source 100. As shown in FIG. 2A, this results in mixing of the spectra 210 and 310, resulting in a combined/third emission spectrum 410. In particular, spectrum 410 is intended to represent a white light, although the combined spectrum 410 may have any appropriate or desired spectral distribution.

As discussed above, all LED devices may be considered to have a lumen depreciation profile. In particular, typical examples, which are hypothetical and are known to vary, for example across different manufacturers, specifications, power output, and especially color exist. Moreover, ageing varies significantly based on how an LED is used. Factors such as junction temperature, junction current, and environmental temperature result in stress that can have an immediate effect on the output of an LED which effect changes over time. Additionally, even under modest stress, LED output changes are to be expected and can be predicted. Light output may be expressed in L-values where L100 is the output measured at T=0, i.e. as measured when the LED is new. Over time, the lumen output of an LED tends to change. In general, the output tends to decrease.

The curve that describes this decrease is referred to herein variously as a profile, depreciation profile, or lumen depreciation profile. A single LED may have multiple profiles depending on the operating or operational stresses expected to be applied to the LED during normal operation.

An LED may be said to be at the end of its useful life when its L-number decreases below a given threshold. For example, a common threshold is considered to be L70 which would define the total lifetime of the LED. However, this 'total lifetime' is arbitrary, and may be much longer than the period of time during which a particular LED is useful in a particular application. In this sense, 'total lifetime' as used herein is specific to a particular LED, and is not related to the effectiveness of the LED in a particular application, in particular where it is used in conjunction with other LEDs.

By contrast, the term 'effective lifetime' is used herein as a measure of the period of time during which one or more LEDs function effectively in a particular application. For example, when the output of a red LED has depreciated to a level that it no longer produces a white light in combination with other LEDs in an array or if a color management control program cannot do any further operational adjustments in order to keep a required white balance, it has exceeded its effective lifetime, even when the output of the LED is still above a certain lumen depreciation value. In this sense, complex calibration systems may for example extend the 'effective lifetime' of the LEDs in an array by adjusting the driving currents of the LEDs in the array to reestablish the correct color balance.

According to an embodiment of the present disclosure, a spectrum-mixing LED light source, in particular a light source having a selectively variable chromaticity, such as a dental light that selectively reduces or eliminates output of blue light, can be achieved according to the exemplary disclosure of FIG. 1 where the lumen depreciation profile of first LED assembly 120 is substantially similar to the lumen depreciation profile of second LED assembly 130. More particularly, the lumen depreciation profiles are advantageously substantially similar over a lifetime, either a total lifetime or an effective lifetime, as those terms are defined above.

Where the term "lumen depreciation profile" does not apply, such as where a fraction of the radiation emitted from the LED assemblies is outside the visible spectrum, the term 'spectral output' or 'total spectral power' may be applied without deviating from the scope of this disclosure. In particular, output measured in lumens or spectral power are subject to similar degradation over time, with the result that the spectral output of an LED diminishes according to a profile that typically differs across LEDs of different types. The terms are therefore used interchangeably here, although one or the other term may not apply in all cases or to a particular embodiment.

The lifetime applicable may advantageously be chosen based on the expected total lifetime of one or more of the components, including LED components used in light source 100, or other independent factors. Advantageously, the applicable lifetime may be chosen to balance cost and reliability. For example, LED assemblies having long life ratings may have a higher initial cost than LED assemblies with steeper lumen depreciation curves and/or spectral output power degradation curves within a given wavelength range. As discussed below, lifetime may also be chosen based on depreciation curve matching, or the availability of appropriate LED assemblies also having similar or substantially similar lumen depreciation profiles and/or spectral output power degradation curves within a given wavelength range.

As used herein, the term 'substantially similar' is to be understood as encompassing any embodiment of first and second LED assemblies 120, 130 wherein their respective lumen depreciation profiles and/or spectral output power degradation curves within a given wavelength range are identical, up to and including embodiments wherein the respective lumen depreciation profiles and/or spectral output power degradation curves within a given wavelength range do not deviate sufficiently over the designated lifespan to alter combined spectrum 410 sufficiently to deviate from a specified standard, such as that defined by a color rendering index (CRI), spectral power output or similar standard.

The respective depreciation profiles or degradation of spectral output of first and second LED assemblies 120 and 130 may also be considered to be substantially similar where they do not deviate from each other by more than 20%, more preferably by not more than 10% still more preferably by not more than 5% or less during the specified lifetime.

In addition to the effect of lumen and/or spectral power depreciation over the lifetime of an LED assembly, instant operating conditions may also have an effect on the output of an LED. Accordingly, it may be advantageous to consider any immediate effect, for example, of temperature on the respective output of first and second LED assemblies 120 and 130 and to match these as well. The immediate relationship between operating conditions and LED output, such as its thermal behavior may also change over the lifetime of the LED. However, where significant deviation in output among LED assemblies may be caused by variations in temperature, selecting LED devices having similar instantaneous thermal behavior or other environmental dependencies for use in a light source such as light source 100 may be advantageous.

As noted above, the respective lumen and/or spectral power depreciation profiles of first LED assembly 120 and second LED assembly 130 may vary depending upon the type and magnitude of stress applied to the assemblies during operation of light source 100. Advantageously, the stresses that have the greatest effect on the magnitude of lumen depreciation should be considered, as well as any differences in operational stresses applied between first and second LED assemblies 120 and 130. Examples of operational stresses include junction temperature, environmental temperature and current density.

As noted above, embodiments of the present disclosure match lumen depreciation profiles and/or spectral power degradation profiles across the at least one first LED assembly 120 with those of the at least one second LED assembly 130 that may be arranged in array 110. In this connection a first LED assembly 120 and second LED assembly 130 may respectively have a lumen maintenance value ($L_m$) being calculated at any given time T (advantageously measured, for example, in hours) according to the formula $L_m = L_a/L_n$, where $L_n$ is the nominal output of a respective LED assembly, referred to herein for example as the output of the LED assembly under operating conditions at T=0, i.e., before any ageing-related lumen depreciation can be detected, and where $L_a$ denotes the actual output of a respective LED assembly.

Where advantageous, a relevant lifetime of light source 100 may be selected by reference to a fixed depreciation of first and/or second LED assemblies 120, 130. For example, light source 100 may have a lifetime defined by the time until $L_m < 70$ in at least one of said first and second LED assembly, as calculated based on tested, measured, or estimated values.

As noted above, the lumen and/or spectral power depreciation profiles of first and second LED assemblies should coincide as closely as possible, but advantageously be at least substantially similar to each other in order to stabilize the spectrum of the output of light source 100. Accordingly, light source 100 may be deemed to coincide, or to be substantially similar when the difference in lumen maintenance value and/or spectral power value for the first LED assembly ($L1_m$) deviates by no more than 20% from the lumen and/or spectral power maintenance value for the second LED assembly ($L2_m$) at any given time in the life of light source 100, or alternately the designated or selected lifetimes of one or both of first and/or second LED assemblies 120, 130.

First LED assembly 120 and second LED assembly 130 have been described in general terms, and reference to lumen depreciation and/or spectral power profiles have been made considering the assemblies themselves. However, first LED assembly 120 may be described in greater detail as including a first LED element 122, such as an LED chip, or chip on board. More particularly, first LED element 122 may be a blue LED chip, or any color LED. Likewise, second LED assembly 130 includes a second LED element 132 which may be an LED chip, or chip on board. Second LED element 132 may be a blue LED chip, or any color LED. According to an embodiment of the present disclosure, $L1_m$ and $L2_m$ are test values of said LED elements, respectively.

Each of the first and second LED assemblies 120, 130, or alternately the first and second LED elements 122, 132 may be subject to operating stresses that impact a lumen and/or spectral power depreciation profile. According to an embodiment of the present disclosure, the operational stress is chosen from a group including junction temperature, environmental temperature and junction current, and is wherein a measured value for said at least one operational stress is within normal operating ranges for said light source. In other words, the LED device is advantageously driven within specified limits.

Further to the individual components included in first LED assembly 120, and according to a further embodiment of the present disclosure, a phosphor converter 124 may advantageously be operatively coupled to first LED element 122. In particular, according to an embodiment of the present disclosure, phosphor converter 124 may be positioned in the path of an output of light from LED element 122. As used herein, the term coupled, or operatively coupled may be interpreted broadly to indicate that phosphor converter 124 is positioned such that light emitted from first LED element 122 is at least partially provided to phosphor converter 124, with or without phosphor converter 124 being fastened, adhered or otherwise affixed to first LED element 122 or placed remotely at a certain distance from the chip surface.

According to a still further embodiment of the present disclosure, and further to individual structures included within first LED assembly 120, a filter 126 may advantageously be provided. In particular, light emitted from first LED element 122 may pass through phosphor converter 124, and thereafter through filter 126. As in the exemplary embodiments including phosphor converter 124, an operative coupling may exist between filter 126 and/or phosphor converter 124 and/or first LED element 122, with a broad interpretation of operative coupling, optionally including a fastening, such as by adhesive, or affixation such as by bonding, or alternative securement of filter 126 within first LED assembly 120, and/or to one or more of first LED element 122 and/or phosphor converter 124.

According to a still further embodiment of the present disclosure, first LED element 122 is a blue LED and phosphor converter 124 that at least partially converts an output of first LED element 122 into a yellow light and where the combination of the light results in a white light. An example of a white light is disclosed in FIG. 2A, having spectral distribution 410.

More particularly, phosphor converter 124 may include a Ce-YAG based yellow phosphor that downconverts a portion of incoming blue light, leaving a portion unconverted. Accordingly, a further exemplary embodiment of the present disclosure is provided where the white light emitted from phosphor converter 124 includes at least a first component of blue light. Exemplary white spectral distribution 410 includes at least a component of blue light, or near or below wavelengths of 450 nanometers.

The quality of white light may be measured against standards approximating the 'ideal' light of daylight. An example of such standards include color rendering index (CRI). According to an embodiment of the present disclosure, a white light may have a high color rendering index (CRI). More particularly, the CRI may be at least 90.

According to a further embodiment of the present disclosure, filter 126 may at least partially block said first component of blue light. This effect is illustrated in FIG. 2B, as ghosted spectrum component 310, which is primarily blue light, blocked for example by filter 126. According to a still further embodiment, filter 126 is a dichroic filter.

By selectively applying power to first power lead 104, first LED assembly 120 may be driven to illuminate. In particular, first LED element 122 begins emitting light, such as a blue light. Phosphor converter at least partially converts the emitted blue light into a spectrum including components 210 and 310 (shown ghosted) as shown in FIG. 2B. However, filter 126 blocks some or all of the blue light, which according to exemplary embodiments of the present disclosure blocks spectrum 310 from the light emitted from first LED assembly 120. In a case where second power lead 106 is not connected to a source of power, light 350 emitted from light source 100 will not include substantial quantities of light having wavelengths in the visible violet/blue spectrum.

According to a further exemplary embodiment of the present disclosure, however, second LED element 132 may be a blue LED. In particular, where LED element 132 produces as second channel 300 of light essentially in the spectrum of 310, application of power to second power lead 106 results in a spectral distribution of light 400 emitted from light source 100 that resembles the white spectrum 410, as shown in FIG. 2A. More particularly, the selection of a blue LED for second LED element 132 permits the selective blocking/adding of visible blue light during operation of light source 100.

Stated another way, the embodiment illustrated in FIG. 2A shows array 110 mixing the light of first channel of visible light 200 and second channel of visible light 300, and wherein second channel of visible light 300 includes a second component 310 of blue light. Advantageously, the second component of blue light is proportional to the first component, blocked by filter 126. When this is the case, the white light emitted from phosphor converter 124 is essentially reconstructed when the first 200 and second 300 channels of visible light are mixed. Accordingly, the white light 400/410 emitted from array 110 in FIG. 2A may have a high CRI. More particularly it may have a CRI of at least 90.

Where first LED element 122 and second LED element 132 have substantially similar lumen depreciation and/or spectral power degradation profiles, any reduction in the output of first LED element 122 due to age is likely to be mirrored in second LED element 132, especially if the same chip technology is used. Accordingly, although the overall lumen output and/or spectral power of light source 100 may decrease over time, the ratio of the relative output of the two light channels will remain largely constant, with the result that the channel 200/400 output 400 of light source 100 remains chromatically stable relative to a multi-LED system in which the various LED elements have divergent lumen depreciation profiles, for example due to different chip technology and operational settings. Moreover, as various exemplary embodiments employ blue LED elements, chromatic stability is further enhanced due to the native stability of blue LEDs compared to LEDs of other colors. This reduces the effect, already of only minor significance, of the unequal illumination-aging of LED elements in light source 100 when the non-curing light mode of FIG. 2B is employed. The use of functionally identical blue LEDs for first and second LED elements 122 and 132 permit the ordinary use of non-curing light mode without substantial risk that first LED assembly 120 will undergo significant lumen or spectral power depreciation during periods of time in which only the first channel of visible light 200 is illuminated.

Still further, and according to an exemplary embodiment of the present disclosure, the use of the same type of LEDs for each of first and second LED elements 122 and 132 is advantageous. As disclosed herein, 'the same type' or 'the same' or 'functionally identical' LED elements are interchangeable terms that denote two or more LEDs that have the same specifications, are of the same manufacture, are from a common batch, made from the same materials or are otherwise indistinguishable when put into ordinary service. Functionally identical, or equivalent LED elements are at least more likely to have identical, or at least substantially similar lumen and/or spectral power depreciation profiles. Accordingly, arrangement of the embodiments of the present disclosure wherein filter 126 removes precisely the spectrum 310 that LED elements 122 and 132 natively produce allows the selective blocking of blue light without populating array 110 with diverse LED elements, which would be more challenging to match for long-term relative chromatic stability.

According to a further embodiment of the present disclosure, a dental light 100 (FIG. 1) is disclosed having an array 110 of light emitting diode (LED) assemblies 122, 132. Array 110 includes at least one first LED assembly 120 housing or including at least one first LED element 122 configured to emit a first light according to a first spectral distribution, (e.g. 310, FIG. 2B). At least one conversion phosphor 124 is fixed within said first light emission, conversion phosphor 124 configured to convert at least a portion of the first spectral distribution to a converted spectral distribution of light (e.g. 410, FIG. 2A). At least one filter 126 is fixed within said converted spectral distribution of emitted light, filter 126 configured to block at least a portion of the converted spectral distribution to emit a filtered spectral distribution of light (e.g. 210, FIG. 2B). A first power lead 104 is connected to said at least one first assembly LED element.

At least one second LED assembly 130 is disclosed having an LED element 132 configured to emit light according to a second spectral distribution, which is advantageously but not necessarily identical to the first spectral distribution (e.g. 310, FIG. 2B). A second power lead 106 is connected to said at least one second assembly LED element.

During operation, the light 200 including the filtered spectral distribution 210 is emitted from array 110 when first power lead 104 is connected to a power source. When both first power lead 104 and second power lead 106 are connected to power, light 400 having a combined spectral distribution 410 including the filtered spectral distribution 210 and the and second spectral distribution 310 is emitted.

As with previous embodiments, the dental light may be based on LED elements including blue LEDs. Where the LEDs are the same kind of LED, that is to say are functionally identical, the first and second spectral distributions will, by definition, be functionally identical as well. Moreover, where filter 126 is configured to block light having spectral distribution 310, precisely the distribution relevant to common dental curing, and where the first and second spectral distributions are also substantially similar, or functionally identical to spectral distribution 310, a dual-mode, 'two spectrum' dental light can advantageously be achieved without employing more than a single kind of LED element.

More particularly, light mixing using LEDs of multiple color is not necessary. In fact, dental light 100 may advantageously be configured such that the converted spectral distribution and the combined spectral distribution are substantially identical, having for example the spectrum 410. Filter 126 simply blocks essentially the same components that are selectively added by the LED elements connected to second power lead 106.

Advantageously, spectrum 410 is a white light. For use in dentistry, the white light may advantageously have a high color rendering index (CRI). More particularly, the CRI may be at least 90. These features may be calibrated on manufacture, and, due to the relative stability in output across the LED components used in the array, (particularly where all the LEDs used are the same) subsequent recalibration may not be needed.

The embodiments thus far disclosed may advantageously employ a method 1000 (FIG. 3) for providing chromatically stable illumination according to an aspect of the present disclosure. For a two-channel system, the method includes providing a first channel of visible light via at least one first LED assembly having a first light output intensity at a first light emission spectrum, and a first lumen and/or spectral power depreciation profile describing the output intensity over a total lifetime of the LED assembly 1010, 1020 includes selecting an effective lifetime within said total lifetime. As discussed above, the selection of an effective lifetime may take into consideration the expected lifetime of the light source, or dental light, as a whole, or may factor in limitations in the selection of components. The effective lifetime is typically the same, or less than the total lifetime of the LED assembly, wherein the total lifetime may itself be defined by an industry convention (LEDs have reached the end of their life at L70, for example), or the total lifetime may be specific to the application in which the LED is used. For example it may be that even a chromatically stable light source no longer meets the needs of a dentist when it produces overall less than some percentage of its nominal, or original output.

In such a case, it is advantageous to consider effective lifetime to be related to the time during which the illumination source may be chromatically stable, and the total lifetime, for purposes of one or more embodiments, to be more closely related to the usability of the device as a whole, even where the color balance may remain true. Although one or more embodiments may achieve and maintain chromatic stability beyond the useful life of the device based on other parameters, selection of an effective lifetime within the total lifetime is likely to be advantageous.

Figure 3:
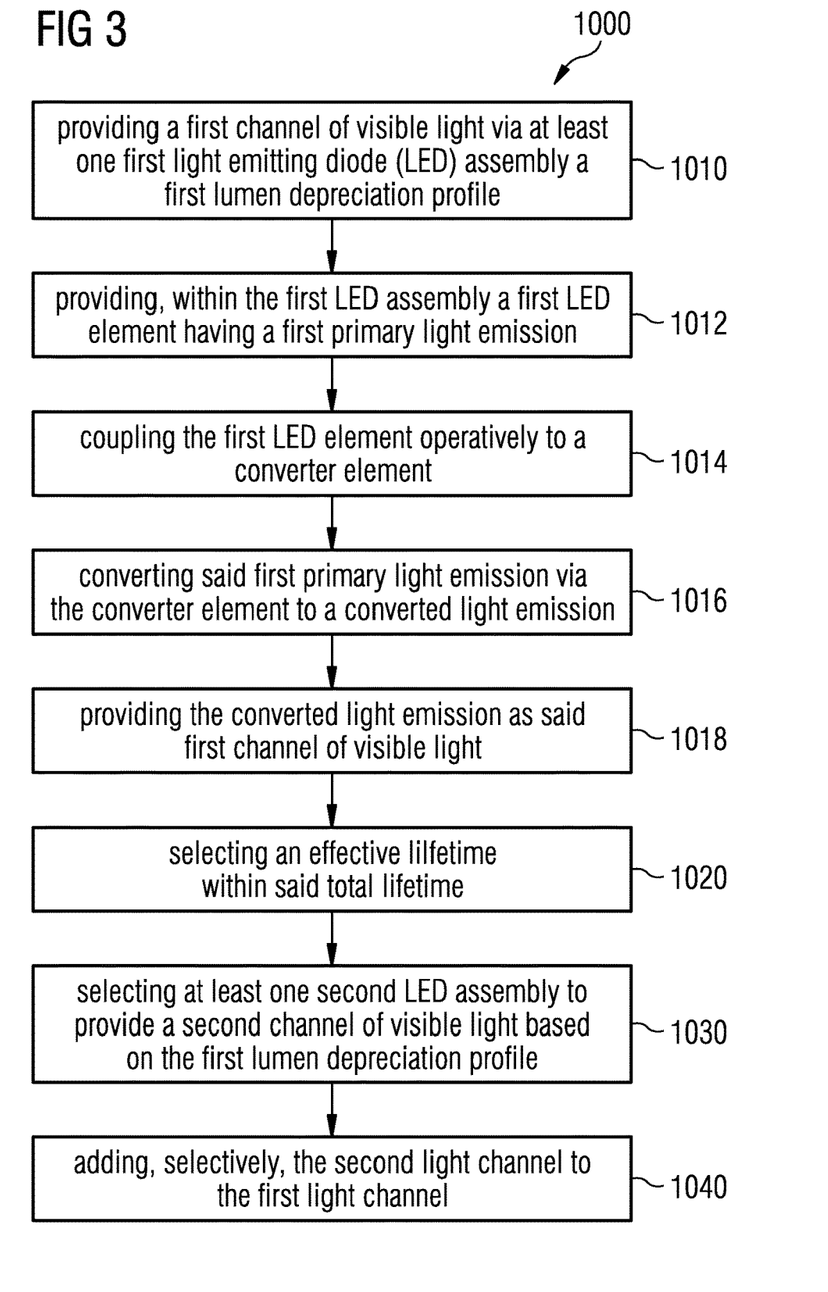
FIG. 3 is a flowchart of a method of the present disclosure.

As disclosed in 1030, at least one second LED assembly is selected to provide a second channel of visible light, the second LED assembly having a second light output intensity at a second light emission spectrum different from said first emission spectrum, and will have a second lumen and/or spectral power depreciation profile describing the intensity of the second light output over time. The second lumen depreciation profile is advantageously substantially similar to said first lumen depreciation profile, during at least said effective lifetime.

Then, in 1040, the second light channel is added selectively to the first light channel. The adding of the two channels may advantageously produce light according to a third emission spectrum, which may advantageously be white light. More particularly, the third emission spectrum may have a high CRI, still more particularly a CRI of at least 90.

The first emission spectrum may advantageously include essentially no blue light in the wavelength range 380 to 450 nm, and the second emission spectrum is essentially blue light in the same wavelength range.

To facilitate mixing of light during the adding of 1040, the at least one first LED assembly may be operatively proximate to the at least one second LED assembly. For purposes of this disclosure, operatively proximate may be understood to be sufficiently close to each other to allow generally homogeneous mixing of the first and second light outputs at an illumination target some distance from the LED assemblies.

The disclosed method may further include 1012-1018, where at 1012, within the first LED assembly a first LED element is provided having a first primary light emission. At 1014 the first LED element is coupled operatively to a converter element, such as a phosphor converter and a filter. At 1016 the first primary light emission is converted via the converter element to a converted light emission, and at 1018 the converted light emission is provided as the first channel of visible light.

Advantageously, particularly for dental applications, the first LED element may be a blue LED. Additionally, the phosphor converter may convert the first primary light emission to a white light including at least a component of the first primary light emission, and advantageously a filter may block at least a portion of that component of the first primary light emission.

A second LED element may be included in the second LED assembly, and the output of the second LED, i.e. its primary light emission, may itself comprise the second channel of light. Where the second LED is also a blue LED, the second LED may also advantageously be functionally identical, i.e. the same kind of LED element as provided for the first LED assembly.

The above embodiments are disclosed both generally as related to a light source, and specifically to a dental light. One or more of the embodiments disclosed above may have particular advantages when used as a dental light, wherein the long term chromatic stability of the two light modes is required, and wherein the white light mode is expected to be in practical use 80%-99% of the service life of the dental light. In white light mode, all LEDs are on. In such a case, differences in aging of the individual LEDs due to the use of the dental light in its "yellow" or "non-curing" mode can be minimized as the non-curing mode is used during the short periods of actually working with uncured composite filling material.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims, and all changes which come within the meaning and range of equivalency of the claims are therefore intended to be embraced.

What is claimed is:

1. A dental light comprising:
an array of light emitting diode (LED) assemblies, the array comprising:
at least one first LED assembly comprising:
at least one first LED element configured to emit a first light according to a first spectral distribution,
at least one conversion phosphor fixed within said first light, the at least one conversion phosphor configured to convert at least a portion of said first spectral distribution to a converted spectral distribution of light,
at least one filter fixed within said converted spectral distribution of light, the at least one filter configured to block at least a portion of the converted spectral distribution to emit a filtered spectral distribution of light, and
a first power lead connected to said at least one first assembly LED element,
at least one second LED assembly comprising:
at least one second LED element configured to emit light according to a second spectral distribution, and
a second power lead connected to said at least one second LED element, wherein light having the filtered spectral distribution is emitted from said array when said first power lead is connected to a power source, and
wherein light having a combined spectral distribution comprising the filtered and second spectral distributions when both first and second power leads are connected to a power source, and
wherein the light emitted from said at least one second LED element is emitted from said at least one second LED assembly without conversion by a phosphor;
wherein said at least one filter is configured to block light having the second spectral distribution; wherein the filter is configured to block light in the range 380-450 nm; and wherein the second LED assembly is configured to emit light in the range 380-450 nm.

2. The dental light of claim 1 wherein said at least one first LED element is a blue LED.

3. The dental light of claim 2 wherein said at least one second LED element is a blue LED.

4. The dental light of claim 1 wherein the filter is a dichroic filter.

5. The dental light of claim 1 wherein the at least one first LED element and the at least one second LED element are substantially functionally identical.

6. The dental light of claim 1 wherein the first spectral distribution and the second spectral distribution are substantially identical.

7. The dental light of claim 1 wherein the converted spectral distribution and the combined spectral distribution are substantially identical.

* * * * *